(12) United States Patent
Wiessler et al.

(10) Patent No.: US 9,217,442 B2
(45) Date of Patent: Dec. 22, 2015

(54) PUMP OR ROTARY CUTTER FOR OPERATION IN A FLUID

(75) Inventors: Petra Wiessler, Berlin (DE); Sven-René Friedel, Berlin (DE); Reiner Liebing, Potsdam (DE); Sami Er, Berlin (DE); Henning Schlicht, Werder (DE)

(73) Assignee: ECP ENTWICKLUNGSGESELLSCHAFT MBH, Berlin (DE)

(*) Notice: Subject to any disclaimer, the term of this patent is extended or adjusted under 35 U.S.C. 154(b) by 16 days.

(21) Appl. No.: 13/261,423

(22) PCT Filed: Mar. 2, 2011

(86) PCT No.: PCT/EP2011/001125
§ 371 (c)(1),
(2), (4) Date: Nov. 14, 2012

(87) PCT Pub. No.: WO2011/107296
PCT Pub. Date: Sep. 9, 2011

(65) Prior Publication Data
US 2013/0066139 A1   Mar. 14, 2013

Related U.S. Application Data

(60) Provisional application No. 61/310,750, filed on Mar. 5, 2010.

(30) Foreign Application Priority Data

Mar. 5, 2010   (EP) .................................... 10075103

(51) Int. Cl.
*A61M 1/10*   (2006.01)
*F04D 29/24*   (2006.01)
(Continued)

(52) U.S. Cl.
CPC ...... *F04D 29/247* (2013.01); *A61B 17/320725* (2013.01); *A61B 17/320758* (2013.01); *A61M 1/101* (2013.01); *A61M 1/1024* (2014.02); *A61M 1/125* (2014.02); *F04D 3/00* (2013.01)

(58) Field of Classification Search
CPC   A61M 1/10; A61M 1/101; A61M 2001/1024
USPC ............................ 623/3.1, 3.13, 3.29; 600/16
See application file for complete search history.

(56) References Cited

U.S. PATENT DOCUMENTS

| 3,510,229 A | 5/1970 | Smith et al. |
| 3,568,659 A | 3/1971 | Karnegis |

(Continued)

FOREIGN PATENT DOCUMENTS

| CA | 1008330 A1 | 4/1977 |
| CA | 2311977 A1 | 12/2000 |

(Continued)

OTHER PUBLICATIONS

English Abstract of CN101448542A.

(Continued)

*Primary Examiner* — Joseph Dietrich
(74) *Attorney, Agent, or Firm* — Ropes & Gray LLP

(57) ABSTRACT

The invention relates to a fluid pump or rotary cutter having at least one first element which can be brought from a transport state into an operating state by changing at least one mechanical property. Such a pump can, for example, be a blood pump for the medical, microinvasive area. The object of achieving a transition between the transport state and the operating state which is as comfortable as possible and in so doing leaving a freedom in the design of the corresponding apparatus, in particular of a pump, which is as large as possible, is achieved using the means of the invention in that the first element at least partly comprises a material or can be filled with a material or material mixture which passes through a chemical reaction, in particular cross-linking, or a crystallization for transition into the operating state.

15 Claims, 6 Drawing Sheets

US 9,217,442 B2

Page 2

(51) Int. Cl.
*A61B 17/3207* (2006.01)
*F04D 3/00* (2006.01)
*A61M 1/12* (2006.01)

(56) References Cited

U.S. PATENT DOCUMENTS

| | | | |
|---|---|---|---|
| 3,802,551 A | 4/1974 | Somers | |
| 3,812,812 A | 5/1974 | Hurwitz | |
| 4,014,317 A | 3/1977 | Bruno | |
| 4,207,028 A | 6/1980 | Ridder | |
| 4,559,951 A | 12/1985 | Dahl et al. | |
| 4,563,181 A | 1/1986 | Wijayarathna et al. | |
| 4,679,558 A | 7/1987 | Kensey et al. | |
| 4,686,982 A | 8/1987 | Nash | |
| 4,747,821 A | 5/1988 | Kensey et al. | |
| 4,749,376 A | 6/1988 | Kensey et al. | |
| 4,753,221 A | 6/1988 | Kensey et al. | |
| 4,801,243 A | 1/1989 | Norton | |
| 4,817,613 A | 4/1989 | Jaraczewski et al. | |
| 4,919,647 A | 4/1990 | Nash | |
| 4,957,504 A | 9/1990 | Chardack | |
| 4,969,865 A | 11/1990 | Hwang et al. | |
| 4,995,857 A | 2/1991 | Arnold | |
| 5,011,469 A | 4/1991 | Buckberg et al. | |
| 5,040,944 A | 8/1991 | Cook | |
| 5,042,984 A | 8/1991 | Kensey et al. | |
| 5,052,404 A | 10/1991 | Hodgson | |
| 5,061,256 A | 10/1991 | Wampler | |
| 5,092,844 A | 3/1992 | Schwartz et al. | |
| 5,097,849 A | 3/1992 | Kensey et al. | |
| 5,108,411 A | 4/1992 | McKenzie | |
| 5,112,292 A | 5/1992 | Hwang et al. | |
| 5,113,872 A | 5/1992 | Jahrmarkt et al. | |
| 5,117,838 A | 6/1992 | Palmer et al. | |
| 5,118,264 A | 6/1992 | Smith | |
| 5,145,333 A | 9/1992 | Smith | |
| 5,163,910 A | 11/1992 | Schwartz et al. | |
| 5,169,378 A | 12/1992 | Figuera | |
| 5,183,384 A | 2/1993 | Trumbly | |
| 5,191,888 A | 3/1993 | Palmer et al. | |
| 5,201,679 A | 4/1993 | Velte, Jr. et al. | |
| 5,275,580 A | 1/1994 | Yamazaki | |
| 5,373,619 A | 12/1994 | Fleischhacker et al. | |
| 5,376,114 A | 12/1994 | Jarvik | |
| 5,501,574 A | 3/1996 | Raible | |
| 5,531,789 A | 7/1996 | Yamazaki et al. | |
| 5,701,911 A | 12/1997 | Sasamine et al. | |
| 5,755,784 A | 5/1998 | Jarvik | |
| 5,776,190 A | 7/1998 | Jarvik | |
| 5,813,405 A | 9/1998 | Montano, Jr. et al. | |
| 5,820,571 A | 10/1998 | Erades et al. | |
| 5,851,174 A | 12/1998 | Jarvik et al. | |
| 5,882,329 A | 3/1999 | Patterson et al. | |
| 5,888,241 A | 3/1999 | Jarvik | |
| 5,938,672 A | 8/1999 | Nash | |
| 6,030,397 A | 2/2000 | Monetti et al. | |
| 6,129,704 A | 10/2000 | Forman et al. | |
| 6,152,693 A | 11/2000 | Olsen et al. | |
| 6,168,624 B1 | 1/2001 | Sudai | |
| 6,254,359 B1 | 7/2001 | Aber | |
| 6,302,910 B1 | 10/2001 | Yamazaki et al. | |
| 6,308,632 B1 | 10/2001 | Shaffer | |
| 6,336,939 B1 | 1/2002 | Yamazaki et al. | |
| 6,346,120 B1 | 2/2002 | Yamazaki et al. | |
| 6,387,125 B1 | 5/2002 | Yamazaki et al. | |
| 6,491,672 B2 | 12/2002 | Slepian et al. | |
| 6,503,224 B1 | 1/2003 | Forman et al. | |
| 6,506,025 B1 | 1/2003 | Gharib | |
| 6,508,787 B2 | 1/2003 | Erbel et al. | |
| 6,517,315 B2 | 2/2003 | Belady | |
| 6,527,521 B2 | 3/2003 | Noda | |
| 6,533,716 B1 | 3/2003 | Schmitz-Rode et al. | |
| 6,537,030 B1 | 3/2003 | Garrison | |
| 6,537,315 B2 | 3/2003 | Yamazaki et al. | |
| 6,592,612 B1 | 7/2003 | Samson et al. | |
| 6,652,548 B2 | 11/2003 | Evans et al. | |
| 6,719,791 B1 | 4/2004 | Nusser | |
| 6,860,713 B2 | 3/2005 | Hoover | |
| 6,945,977 B2 | 9/2005 | Demarais et al. | |
| 6,981,942 B2 | 1/2006 | Khaw et al. | |
| 7,022,100 B1 | 4/2006 | Aboul-Hosn et al. | |
| 7,027,875 B2 | 4/2006 | Siess et al. | |
| 7,074,018 B2 | 7/2006 | Chang | |
| 7,179,273 B1 | 2/2007 | Palmer et al. | |
| 7,393,181 B2 | 7/2008 | McBride et al. | |
| 7,467,929 B2 | 12/2008 | Nusser et al. | |
| 7,648,619 B2 * | 1/2010 | Chuang et al. | 417/48 |
| 7,731,675 B2 | 6/2010 | Aboul-Hosn et al. | |
| 7,878,967 B1 * | 2/2011 | Khanal | 600/16 |
| 7,927,068 B2 | 4/2011 | McBride et al. | |
| 7,934,909 B2 | 5/2011 | Neusser et al. | |
| 7,942,804 B2 * | 5/2011 | Khaw | 600/16 |
| 8,048,086 B2 | 11/2011 | Lee-Sepsick et al. | |
| 8,052,669 B2 | 11/2011 | Lee-Sepsick et al. | |
| 2002/0123661 A1 | 9/2002 | Verkerke et al. | |
| 2003/0135086 A1 | 7/2003 | Khaw et al. | |
| 2003/0231959 A1 | 12/2003 | Snider | |
| 2004/0044266 A1 | 3/2004 | Siess et al. | |
| 2004/0046466 A1 | 3/2004 | Siess et al. | |
| 2004/0093074 A1 | 5/2004 | Hildebrand et al. | |
| 2004/0215222 A1 | 10/2004 | Krivoruchko | |
| 2004/0215228 A1 | 10/2004 | Simpson et al. | |
| 2006/0008349 A1 | 1/2006 | Khaw | |
| 2006/0062672 A1 | 3/2006 | McBride et al. | |
| 2006/0195004 A1 | 8/2006 | Jarvik | |
| 2008/0132747 A1 | 6/2008 | Shifflette | |
| 2008/0262584 A1 | 10/2008 | Bottomley et al. | |
| 2008/0306327 A1 | 12/2008 | Shifflette | |
| 2009/0060743 A1 | 3/2009 | McBride et al. | |
| 2009/0093764 A1 | 4/2009 | Pfeffer et al. | |
| 2009/0093796 A1 | 4/2009 | Pfeffer et al. | |
| 2009/0234278 A1 | 9/2009 | Eck | |
| 2010/0036360 A1 | 2/2010 | Herbowy et al. | |
| 2010/0041939 A1 | 2/2010 | Siess | |
| 2010/0268017 A1 | 10/2010 | Siess | |
| 2011/0236210 A1 | 9/2011 | McBride et al. | |
| 2011/0238172 A1 | 9/2011 | Akdis | |
| 2011/0275884 A1 | 11/2011 | Scheckel | |
| 2012/0016456 A1 | 1/2012 | Herbowy et al. | |
| 2012/0039711 A1 | 2/2012 | Roehn | |
| 2012/0041254 A1 | 2/2012 | Scheckel | |
| 2012/0046260 A1 | 2/2012 | Lee-Sepsick et al. | |
| 2012/0046648 A1 | 2/2012 | Scheckel | |
| 2012/0093628 A1 | 4/2012 | Liebing | |
| 2012/0101455 A1 | 4/2012 | Liebing | |
| 2012/0142994 A1 | 6/2012 | Toellner | |
| 2012/0184803 A1 | 7/2012 | Simon et al. | |
| 2012/0224970 A1 | 9/2012 | Schumacher et al. | |
| 2012/0234411 A1 | 9/2012 | Scheckel | |
| 2012/0237353 A1 | 9/2012 | Schumacher et al. | |
| 2012/0237357 A1 | 9/2012 | Schumacher et al. | |
| 2012/0264523 A1 | 10/2012 | Liebing | |
| 2012/0265002 A1 | 10/2012 | Roehn et al. | |
| 2012/0294727 A1 | 11/2012 | Roehn | |
| 2012/0301318 A1 | 11/2012 | Er | |
| 2012/0308406 A1 | 12/2012 | Schumacher | |
| 2013/0019968 A1 | 1/2013 | Liebing | |
| 2013/0041202 A1 | 2/2013 | Toellner | |
| 2013/0060077 A1 | 3/2013 | Liebing | |
| 2013/0066139 A1 | 3/2013 | Wiessler et al. | |
| 2013/0085318 A1 | 4/2013 | Toellner | |
| 2013/0177409 A1 | 7/2013 | Schumacher et al. | |
| 2013/0177432 A1 | 7/2013 | Toellner | |
| 2013/0204362 A1 | 8/2013 | Toellner | |
| 2013/0237744 A1 | 9/2013 | Pfeffer et al. | |
| 2014/0039465 A1 | 2/2014 | Schulz et al. | |

FOREIGN PATENT DOCUMENTS

| | | |
|---|---|---|
| CA | 2701809 A1 | 4/2009 |
| CA | 2701810 | 4/2009 |
| CN | 101448542 A | 6/2009 |
| CN | 102834126 A | 12/2012 |
| DE | 2207296 A1 | 8/1972 |

(56) References Cited

FOREIGN PATENT DOCUMENTS

| | | |
|---|---|---|
| DE | 2113986 A1 | 9/1972 |
| DE | 2233293 A1 | 1/1973 |
| DE | 2613696 A1 | 10/1977 |
| DE | 4124299 A1 | 1/1992 |
| DE | 69103295 T2 | 12/1994 |
| DE | 19535781 A1 | 3/1997 |
| DE | 19711935 A1 | 4/1998 |
| DE | 69407869 T2 | 4/1998 |
| DE | 29804046 U1 | 6/1998 |
| DE | 69017784 T3 | 4/2000 |
| DE | 69427390 T2 | 9/2001 |
| DE | 10059714 C1 | 5/2002 |
| DE | 10108810 A1 | 8/2002 |
| DE | 10155011 A1 | 5/2003 |
| DE | 69431204 T2 | 8/2003 |
| DE | 10336902 B3 | 8/2004 |
| DE | 102010011998 A1 | 9/2010 |
| EP | 0480102 A1 | 4/1992 |
| EP | 0560000 A2 | 9/1993 |
| EP | 0629412 B1 | 1/1998 |
| EP | 0884064 A2 | 12/1998 |
| EP | 0916359 A1 | 5/1999 |
| EP | 1066851 A1 | 1/2001 |
| EP | 0914171 B1 | 10/2001 |
| EP | 0768091 B1 | 7/2003 |
| EP | 0951302 B1 | 9/2004 |
| EP | 1114648 B1 | 9/2005 |
| EP | 1019117 B1 | 11/2006 |
| EP | 1337288 B1 | 3/2008 |
| EP | 2218469 A1 | 8/2010 |
| EP | 2229965 A1 | 9/2010 |
| EP | 2301598 A1 | 3/2011 |
| EP | 2308524 A1 | 4/2011 |
| EP | 2343091 A1 | 7/2011 |
| EP | 2345440 A1 | 7/2011 |
| EP | 2366412 A2 | 9/2011 |
| EP | 1651290 B1 | 1/2012 |
| EP | 2497521 A1 | 9/2012 |
| EP | 2606919 A1 | 6/2013 |
| EP | 2606920 A1 | 6/2013 |
| EP | 2607712 A1 | 6/2013 |
| GB | 536 245 A | 5/1941 |
| GB | 2239675 A | 7/1991 |
| RU | 2229899 C2 | 6/2004 |
| WO | 9202263 A1 | 2/1992 |
| WO | 9302732 A1 | 2/1993 |
| WO | 9303786 A1 | 3/1993 |
| WO | 9314805 A1 | 8/1993 |
| WO | 9401148 A1 | 1/1994 |
| WO | 9405347 A1 | 3/1994 |
| WO | 9409835 A1 | 5/1994 |
| WO | 9420165 A2 | 9/1994 |
| WO | 9523000 A2 | 8/1995 |
| WO | 9618358 A1 | 6/1996 |
| WO | 9625969 A2 | 8/1996 |
| WO | 9744071 A1 | 11/1997 |
| WO | 9853864 A1 | 12/1998 |
| WO | 9919017 A1 | 4/1999 |
| WO | 0027446 A1 | 5/2000 |
| WO | 0043054 A2 | 7/2000 |
| WO | 0062842 | 10/2000 |
| WO | 0107760 A1 | 2/2001 |
| WO | 0107787 A1 | 2/2001 |
| WO | 0183016 A2 | 11/2001 |
| WO | 03057013 A2 | 7/2003 |
| WO | 03103745 A2 | 12/2003 |
| WO | 2005002646 A1 | 1/2005 |
| WO | 2005016416 A1 | 2/2005 |
| WO | 2005021078 A1 | 3/2005 |
| WO | 2005030316 A1 | 4/2005 |
| WO | 2005032620 A1 | 4/2005 |
| WO | 2005081681 A2 | 9/2005 |
| WO | 2006020942 A1 | 2/2006 |
| WO | 2006034158 A2 | 3/2006 |
| WO | 2006133209 A1 | 12/2006 |
| WO | 2007003351 A1 | 1/2007 |
| WO | 2007103390 A2 | 9/2007 |
| WO | 2007103464 A2 | 9/2007 |
| WO | 2007112033 A2 | 10/2007 |
| WO | WO 2007/135577 A2 | 11/2007 |
| WO | 2008017289 A2 | 2/2008 |
| WO | 2008034068 A2 | 3/2008 |
| WO | 2008054699 A2 | 5/2008 |
| WO | 2008106103 A2 | 9/2008 |
| WO | 2008116765 A2 | 10/2008 |
| WO | 2008124696 A1 | 10/2008 |
| WO | 2008137352 A1 | 11/2008 |
| WO | 2008137353 A1 | 11/2008 |
| WO | 2009015784 A1 | 2/2009 |
| WO | WO 2009/132309 A1 | 10/2009 |
| WO | 2010133567 A1 | 11/2010 |
| WO | 2013034547 A1 | 3/2013 |
| WO | 2013092971 A1 | 6/2013 |
| WO | 2013093001 A2 | 6/2013 |
| WO | 2013093058 A1 | 6/2013 |

OTHER PUBLICATIONS

English Abstract of CN102834126A.

* cited by examiner

PUMP OR ROTARY CUTTER FOR OPERATION IN A FLUID

BACKGROUND OF THE INVENTION

The invention is in the field of mechanical engineering and precision engineering and can be used to particular advantage in apparatus which are conveyed to a deployment site in a transport state and are there brought into an operating state before they are started.

This is, for example, sensible with devices which have to be conveyed to sites which are difficult to access in order to be used there, for example pumps or machining tools in contorted hose systems or pipe systems.

In the microscopic scale, such devices can be used as microinvasive devices, for example pumps or rotary cutters in human or animal vessels, for example blood vessels or other bodily cavities.

In this respect, it is difficult to introduce these devices through the body's own vessels since the corresponding dimensions have to be kept very small for this purpose, with simultaneously larger dimensions being sensible in operation for the efficiency of use.

In the field of catheter pumps, in particular of blood pumps, radially compressible pumps have already been proposed to solve this problem which are kept in a transport state with small radial extent during transport and which can be radially expanded at the deployment site, for example in a ventricle, after introduction there.

For this purpose, complex and/or expensive mechanical constructions are known which serve the erection of conveying elements of a rotor. In addition, it is often necessary to stabilize the corresponding conveying elements such as conveying blades in operation since they are exposed to considerable fluid forces in operation.

A compressible rotor is known, for example, from U.S. Pat. No. 6,860,713. In addition, a further rotor is known from U.S. Pat. No. 7,393,181 B2. In the solutions known from the patent literature, provision is made in part that a rotor is compressible by elastically deformable conveying blades or that erection mechanisms for conveying blades are provided which are otherwise laid at the side of the rotor when it is stationary.

In addition to the compressibility of the rotor, it can also be advantageous or sensible to configure the pump housing, which can surround the rotor, in a correspondingly compressible manner.

In this respect, there is as a rule the problem that, on the one hand, the construction and the materials of the rotor should be stable in operation in order reliably to convey the fluid at high speeds and that, on the other hand, a certain yielding of at least parts of the rotor is desirable to keep the forces which are necessary for the compression of the rotor or of the pump within limits.

A technique is known from WO 2009/132309 to bring stents into a desired form after the introduction into a blood vessel by introducing a hardenable medium and subsequently to stabilize them in an operating state.

BRIEF SUMMARY OF THE INVENTION

It is the underlying object of the present invention against this background to configure a corresponding apparatus for a mechanical action on a medium, in particular on a fluid pump or a rotary cutter, such that it can be sensibly brought from a transport state into an operating state, wherein the transport state has a particular suitability for transport, whereas the operating state differs from this and is in particular suitable for the operation of the apparatus/pump.

The object is achieved by the features of the invention in accordance with claim 1.

Since the first element comprises a material or is filled or fillable with a material or a material mixture which passes through a chemical reaction on transition into the operating state, for example a cross-linking or a transition from the liquid state into a solid state or a change in the rheological state and thus at least changes a mechanical property, it is possible to implement a lower stiffness or a lower viscosity in the transport state of the first element, for example, than in the operating state. For example, the first element can be a conveying element, for example a conveying blade of a rotor of a fluid pump or a bracing element of a rotary cutter so that, on a lower stiffness, the corresponding conveying element can be laid onto a hub and the corresponding rotor is thus easily compressible. In this state, the rotor can also be self-compressible in that, in the state of rest, the conveying elements lie on the hub and are only erected on being put into operation by centrifugal forces.

In order then to ensure a higher stiffness of the conveying blades or conveying elements in operation, the material of which the conveying blade or a part of the conveying blade is composed is selected such that it undergoes a hardening or stiffening when passing through the corresponding reaction or the transition, in particular the transition into a different state of aggregation, for example a crystallization.

Provision can also be made that the first element, that is, for example, the conveying element, has hollow spaces which can be filled with a corresponding material, for example via feed hoses, and which can then be hardened, stiffened or, when it is a case of a liquid, whose viscosity can be changed.

The change of the viscosity can be effected, for example with magnetorheological or electrorheological liquids, by applying a magnetic field or an electric field from outside a patient's body. A corresponding field can, however, also be effected by coils or electrodes in the body in the direct vicinity of the pump/rotary cutter. The field generating elements can also be directly fastened to the pump/rotary cutter.

In this respect, it is not the whole element which has to change its properties accordingly, but it is rather sufficient, for example, if a joint connecting the conveying element to a hub is stiffened by the corresponding reaction or changes its shape and thereby radially expands or erects the conveying element.

Provision can also be made that the first element represents another part of a rotor of a fluid pump or that a pump housing has accordingly to be brought into an operating shape or a stiffness corresponding to the operation.

In this case, as with a corresponding use with a rotor, hollow spaces can also be provided which can, for example, be filled with a fluid under pressure and can thus be inflated to give the corresponding first element a desired shape, whereupon the material can be hardened or stiffened to keep this shape stable.

Alternatively to the stiffness, a different mechanical property such as the geometrical shape or size can be changed by the corresponding reaction. For example, a part of a conveying blade can be shorted or extended in the manner of a shrinking hose by the reaction and thereby, that is, by means of lever forces, erect or stiffen the conveying blade.

The material of which the first element is composed in part or with which it can be filled, can, for example, be a hardenable material, in particular a hardenable plastic.

A hardening can take place for transition into the operating state, for example by temperature effect or pressure effect, electric and/or magnetic fields or pulses, radiation (IR light or UV light, α, β, γ radiation), mechanical effect, e.g. ultrasound or vibration, or can also be brought about by contact with a further material or by initialization of a crystallization with a liquid material.

The further material can in this respect be a real reaction partner which likewise reacts in the reaction and undergoes a conversion or it can be a catalyst or enzyme which, when added, results in an acceleration of the reaction.

The further material can, for example, be included in the medium on which the apparatus should act, for example in the body fluid in which a corresponding fluid pump should be operated. In this case, the body fluid can diffuse on the introduction of the apparatus into a body and the desired reaction can then take place before the start of operation either automatically or initiated or assisted by additional measures. The first material can for this purpose e.g. comprise a protein or consist of a protein.

It becomes possible by the invention to ensure mechanical properties for the operation of the apparatus, for example the pump, which would be disadvantageous during the transport to the deployment site and which can be avoided by the invention. These properties are only achieved after the bringing to the deployment site with the end of the corresponding reactions. The corresponding reactions can be reversible, but also irreversible.

An advantageous embodiment of the invention further provides that the first element can be changed by a continued or further reaction, reversibly or irreversibly, into a state in which the apparatus can be transported or in which it can be brought into a transport state by mechanical destruction.

For example, by continuing the reaction which was passed through before the operating state was reached, a further change of the mechanical properties can take place, e.g. by (cross-linking) embrittlement of the material of which the first element is wholly or partly composed. This embrittlement can, for example, go so far with a synthetic resin that the corresponding parts can break by themselves or can at least be easily broken in order again to achieve a suitable transport state for the return transport of the apparatus/fluid pump. A different reaction can, however, also be provided to achieve the corresponding desired result.

In addition to the apparatus in accordance with the invention, the invention also relates to a method in which the apparatus is first introduced into a body of a living being, wherein the material/the material mixture of the first element thereupon undergoes a reaction, in particular a cross-linking, or a crystallization from the liquid phase, before the apparatus is started.

By such a handling, the apparatus is first brought to the deployment site within a body of a living being in the transport state and is only there brought into the operating state with respect to the mechanical properties and thus into a form efficient for operation.

Provision can particularly advantageously be made that the or a material is introduced into at least one hollow space of the first element before the reaction.

For example, a hollow space or a series of hollow spaces, which can be formed, for example, by bubbles of a foam of which the first element is composed, can be filled via hoses with a material which can either itself pass through a reaction to change its mechanical properties or which meets a further material in the hollow spaces and reacts accordingly with it, or wherein one of the materials serves as a catalyst for the reaction.

The actual reaction can in this respect be initiated, assisted or carried out by a corresponding influencing from outside, wherein, for example, radiation, temperature change, mechanical action, such as ultrasound, or the action by electric and/or magnetic fields can serve for this purpose.

The invention moreover relates to a fluid pump or rotary cutter having at least one first element which can be brought from a transport state into an operating state by changing at least one mechanical property, wherein the first element at least partly comprises a material or can be filled with a material or material mixture which, as long as it is exposed to a radiation or an electric and/or magnetic field, has mechanical properties, in particular with respect to stiffness, viscosity, size and/or shape, changed compared with the state without such an action.

Examples for such a change of the mechanical properties by fields are the piezoelectric effect and magnetorestriction or with liquids the magnetorheological effect or the change of the viscosity by electric field effect.

A corresponding method in accordance with the invention for putting such an apparatus into operation provides that the apparatus is exposed to the corresponding action to make the apparatus operable after its introduction into a body of a living being. The action usually has to be maintained during the operation of the apparatus/fluid pump. Neither a reversible nor an irreversible chemical reaction has to take place in this respect, but rather only a different mechanical state of the material is adopted in dependence on the action.

In a modification, the invention can also be configured so that the corresponding action is maintained in the transport state and is removed or is omitted for reaching or during the operating state.

Different mechanisms usable in situ can be considered for the direct change of the mechanical properties of the mentioned elements, in particular the elements of pumps and rotary cutters, including mechanisms in the chemical field, in particular cross-linking. Cross-linking in macromolecular chemistry refers to reactions in which a plurality of individual macromolecules are linked to form a three-dimensional network. The linking can be achieved either directly on the buildup of the macromolecules or by reactions on already existing polymers. Examples for directly cross-linking reactions are radical polymerizations of monomers having two vinyl functions or the polycondensation or polyaddition using monomers having two or more functional groups. The cross-linking of already existing polymers can take place either via functional groups already present in the polymer by an adroit choice of the reaction conditions (so-called self cross-linkers) or by the addition of multifunctional low-molecular substances, the cross-linking agents. The hardening of epoxy resins using amines and the addition of substances containing sulfur on the vulcanization of rubber are examples for cross-linking reactions.

Generally synthetic resins, polyvinyl chloride (PVC), vulcanized rubber, polyethylene, PMMA, polypropylene, PET, PTFE, polyurethanes, polyesters, polyamides, polystyrene and proteins (example: keratin) are known as cross-linkable materials. The biocompatibility naturally has to be considered on the selection for the use in accordance with the invention. Optionally, less suitable materials can only be used as a filling for hollow bodies.

The individual material classes in detail:

In accordance with DIN 55958, synthetic resins (also called reaction resin) are synthetically manufactured by polymerization reactions or polycondensation reactions. They can be modified by natural substances, for example vegetable or animal oils or natural resins, or manufactured by esterification or saponification of natural resins.

Synthetic resins as a rule comprise two main components. The mixture of both parts (resins and hardeners) produces the reactive resin compound. The reaction process is largely dependent on the environmental temperature and the material composition can often be selected so that the hardening reaction only takes place at a noticeable speed on a heating to body temperature. On hardening, the viscosity increases and when the hardening is complete a non-meltable (thermosetting) plastic is obtained.

A polymerization can also be initiated in a variety of plastics by the application of radiation (particle radiation (alpha or beta particles), or also X-ray radiation or gamma radiation or UV radiation). There are, e.g. in dental engineering, excellent UV-hardening adhesives which are also correspondingly biocompatible.

Radiation cross-linking gives inexpensive bulk plastics or technical plastics the mechanical, thermal and chemical properties of high-performance plastics. This refining of plastics allows a use under conditions which these plastics would otherwise not withstand. The high-energy beta or gamma radiation triggers chemical reactions in the plastic parts and thus results in a cross-linking of the molecules—comparable to vulcanization in rubbers.

The cross-linking of polyethylene, polyamide, PVC and PBT is the most significant from a quantity aspect.

The cross-linking of thermoplastic elastomers (TPO, TPC and TPA) is increasingly gaining importance. A cross-linking of polypropylene is generally also possible although degradation reactions predominate with this material as a rule. The following can apply as a general rule: Radiation cross-linking is always possible when chemical cross-linking by means of radical initiators such as peroxides is possible.

The advantage of radiation cross-linking is that the method works at room temperature or at body temperature and at normal pressure.

The radiation for hardening takes place after or during the molding or deforming. A direct deforming can, however, also take place by the radiation itself and by an accompanying cross-linking and desired shrinking or stretching of the material thus treated. The advantageous processing properties of thermoplastics are thus combined with the properties of thermosetting systems.

Rubber is mainly manufactured synthetically. Synthetic rubber is usually composed of styrene and butadiene; other raw material bases are styrene acrylate, pure acrylate, vinyl acetate. The first commercially usable one was the styrene butadiene rubber, another is neoprene.

Polyethylene (abbreviation PE) is a thermoplastic manufactured by polymerization of ethene.

Polyethylene belongs to the group of polyolefins. Known trade names include: Alathon, Dyneema, Hostalen, Lupolen, Polythen, Spectra, Trolen, Vestolen. Polyethylene is manufactured on the basis of ethylene gas which can be manufactured either conventionally in a petrochemical manner or from ethanol.

Polyurethanes (PU, DIN abbreviation: PUR) are plastics or synthetic resins which arise from the polyaddition reaction of diolen or polyolene with polyisocyanates. The urethane group is characteristic for polyurethanes.

Polyurethanes can be hard and brittle, or also soft and elastic, depending on the manufacture. The elastomers in particular show a comparatively high breaking strength. In foamed form, polyurethane is known as a permanently elastic flexible foam or as a hard expanding foam.

Polyurethanes can have different properties depending on the choice of the isocyanate and of the polyol. The density of unfoamed polyurethane varies between around 1000 and 1250 kg/m3.

The later properties are substantially determined by the polyol component because it is usually not the isocyanate component which is adapted to achieve the desired properties, but rather the polyol component. The following isocyanate components are generally used:
methylene diphenyl diisocyanate (MDI)
polymeric methylene diphenyl diisocyanate (PMDI)
toluene diisocyanate (TDI)
napththylene diisocyanate (NDI)
hexamethylene diisocyanate (HDI)
isophorone diisocyanate (IPDI)
4,4'-dicyclohexylmethane diisocyanate (H12MDI)

Mechanical properties can be influenced in dependence on the chain length and on the number of branches in the polyol. A use of polyester polyols in addition to the more usual polyether polyols results in better stability because polyester polyols have a higher melting point and thus solidify on application of the polyurethane.

The foaming of polyurethane foams arises due to the addition of water. On the reaction of water with isocyanate, carbon dioxide is split off which swells the foam. The volume weight of the arising foam can be varied by the quantity of added water. Typical densities are around 5 to 40 kg/m3 for soft slab foam or 30 to 90 kg/m3 for hard slab foam.

When polyurethanes are fully cured and no longer contain any monomers, they as a rule do not have any properties harmful to the health. Isocyanates can, however, trigger allergies and are suspected of causing cancer. The toluene diisocyanate used for some polyurethanes evaporates at room temperature and can cause damage in the lung when inhaled. Such substances are predominantly only used as filling of a closed hollow body, with subsequent hardening, located in the patient's body.

Polyurethanes arise by the polyaddition reaction of polyisocyanates with multiple alcohols, the polyols. The linking takes place by the reaction of an isocyanate group (—N=C=O) of a molecule having a hydroxyl group (—OH) of another molecule while forming a urethane group (—NH—CO—O—). In this respect, no splitting off of secondary products takes place such as in polycondensation.

The polyurethane formation by polycondensation requires at least two different monomers, in the simplest case diol and diisocyanate. It takes place in stages. First, a bifunctional molecule having an isocyanate group (—N=C=O) and a hydroxyl group (—OH) is formed from diol and diisocyanate. It can react at both ends with further monomers. In this respect, short molecule chains arise, so-called oligomers. They can react with further monomers, other oligomers or already formed polymers.

Depending on the starting materials, linear or cross-linked polymers are obtained. Linear polyurethanes can, for example, be obtained from diols and diisocyanates. Linear polyurethanes can be subsequently cross-linked by addition of further diisocyanate. Alternatively, cross-linked polyurethanes can also be manufactured by the reaction of diisocyanates or triisocyanates with polyols.

In a secondary reaction, water reacts with some isocyanate groups; in so doing, carbon dioxide is released which allows the still soft plastic to swell. The simultaneously created primary amino group reacts with an isocyanate group to form a substituted urea.

If a specific polyurethane should be manufactured in practice, two possibilities are available:
Direct reaction of a polyol with a polyisocyanate (a one-stage process)
Manufacturing a functionalized smaller polymer (so-called prepolymer) as an intermediate product which reacts in a second step to form the desired polymer by cross-linking the functional groups (a two-stage process)

Biogenic Polyols

As a rule, both the polyols and the polyisocyanates originate from the production from petrochemical raw materials; however, polyols on the basis of vegetable oils can also be used. *Ricinus* oil is above all suitable for this purpose since it has hydroxyl groups itself and it can be converted directly with isocyanates. Derivatives of the *ricinus* oil can furthermore be used. Furthermore, polyols on the basis of vegetable oils can be manufactured, on the one hand, by epoxidation of the vegetable oils with a subsequent ring opening and via a transesterification of vegetable oils with glycerin. Polyurethanes on the basis of vegetable oils are also marketed as "bio polyurethanes" due to the biogenic origin of some of the raw materials.

Polyesters are polymers having ester functions —[—CO—O—]— in their main chain. Polyesters admittedly are also present in nature, but today polyesters are rather understood as a large family of synthetic polymers (plastics) which include the widely used polycarbonates (PC) and above all the technically important thermoplastic polyethylene terephthalate (PET). Mylar is a particular processing form of the polyethylene enterephthalate—as a film. A further form is the thermosetting unsaturated polyester resin (UP) which is used as an inexpensive matrix resin in the field of fiber plastic composites.

The following can be considered as the polyester:
PES or PEs polyester (group name)
PBT polybutylene terephthalate, a derivative of terephthalic acid
PC polycarbonate, a derivative of carbonic acid
PET polyethylene terephthalate, a derivative of terephthalic acid
PEN polyethylene naphthalate
UP unsaturated polyester resin
polyamides The designation polyamides is usually used as a name for synthetic technically usable thermoplastics and thus delineates this material class from the chemically related proteins. Almost all important polyamides are derived from primary amines, that is, the functional group —CO—NH— occurs in their repetition units. In addition, polyamides of secondary amines (—CO—NR—, R=organic residue) also exist. In particular amino carboxylic acids, lactams and/or diamines and dicarboxylic acids are used as monomers for the polyamides.

Polyamides can be categorized in the following classes:
By the Kind of Monomers

Aliphatic polyamides: the monomers are derived from aliphatic base bodies, e.g. PA from ε-caprolactam (polycaprolactam, abbreviated PA 6) or from hexamethylene diamine and adipic acid (PA 66).

Partially aromatic polyamides: the monomers are derived in part from aromatic base bodies, e.g. PA from hexamethylene diamine and terephthalic acid (PA 6T).

Aromatic polyamides (polyaramides): the monomers are derived from purely aromatic base bodies, e.g. para-phenylene diamine and terephthalic acid (aramide).

By the Kind of Monomer Composition

Homopolyamides: the polymer is derived from an amino carboxylic acid or from a lactam or a diamine and an dicarboxylic acid. Such polyamides can be described by a single repetition unit. Examples for this are the PA from caprolactam [NH—(CH2)5-CO]n (PA 6) or the PA from hexamethylene diamine and adipic acid [NH—(CH2)6-NH—CO—(CH2)4-CO]n (PA 66).

Copolyamides: the polyamide is derived from a plurality of different monomers. Such polyamides can only be described by giving a plurality of repetition units. Examples for this are the PA from caprolactam, hexamethylene diamine and adipic acid [NH—(CH2)6-NH—CO—(CH2)4-CO]n-[NH—(CH2)5-CO]m (PA 6/66), or PA from hexamethylene diamine, adipic acid and sebacic acid [NH—(CH2)6-NH—CO—(CH2)4-CO]n-[NH—(CH2)6-NH—CO—(CH2)8-CO]m (PA 66/610). It must be noted that the formulae given only describe the polymer composition, but not the sequence of the monomer units; these are usually statistically distributed over the polymer chains.

By the Kind of Softening/Solidification Behavior

Partially crystalline polyamides: form crystalline domains from the melt when cooling (1st order phase transition). As a rule, the whole melt does not solidify in a crystalline manner, but amorphous domains are rather also formed (see below). The ratio between the crystalline and the amorphous domains is determined by the chemical nature of the polyamide and by the cooling conditions. In addition, the crystallization can be promoted or hindered by nucleating or antinucleating additives. Polyamides which crystallize easily are e.g. PA 46 or PA 66; polyamides which crystallize with difficulty are e.g. PA mXD6 from xylylene diamine and adipic acid or certain copolyamides.

Amorphous polyamides: solidify in glass-like manner from the melt. In the solid state, there is no long-range order of the repetition units. The transition between solid and liquid is described by the glass transition temperature (2nd order phase transition). Examples are the PA from hexamethylene diamine and isophthalic acid (PA 6I) and certain copolyamides. Generally, amorphous polyamides include monomer units which make a regular, crystalline arrangement of the chains impossible. Under extreme cooling conditions, otherwise partially crystalline polyamides can also solidify amorphously.

Polystyrene (abbreviation PS, IUPAC name: poly(1-phenylethane-1,2-diyl)) is a transparent, amorphous or partly crystalline thermoplastic. Amorphous polystyrene can be used for a variety of purposes.

Polystyrene is used either as a thermoplastically processable material or as a foam (expanded polystyrene). Polystyrene is physiologically harmless. Polystyrene is predominantly gained by suspension polymerization of the monomer styrene which has exceptional polymerization properties. It can be polymerized radically, cationically, anionically or by means of Ziegler-Natta catalysts. Ethene is today acquired from crude oil. Chlorine is above all acquired on a large technical scale in chlorine alkaline electrolysis from common salt. The chlorine is added to the ethene in a first step and 1,2-dichloroethene is created. In a second step, HCl is split off therefrom, with VCM arising. VCM is polymerized in an autoclave to form PVC under pressure and under the addition of initiators and other additives. Three different polymerization processes are essentially known. The oldest process, in a historical view, is emulsion polymerization. The initiators (for example peroxides and other per compounds) are soluble in water in this case. The so-called E-PVC is obtained. If the VCM is distributed in the water by intensive stirring and if the initiator (for example organic peroxides, azobisisobutyronitrile [AIBN]) is soluble in monomers, one speaks of suspension polymerization which results in S-PVC. If no water is used during the polymerization, one speaks of block PVC or mass PVC, also called M-PVC. In this respect, the initiator is dissolved in monomeric vinyl chloride.

Magnetorheological Liquids:

The liquid used, a special magnetorheological oil, is permeated with microscopically small, magnetically polarizable metal particles. It is possible to generate a magnetic field via an electromagnet or a permanent magnet. The metal particles are thereby aligned in the direction of the magnetic field and thus decisively influence the viscosity, i.e. the flowability of the oil. By applying a voltage, the arrangement of the magnetic particles and thus the physical consistency (viscosity) of the liquid reacting almost without delay is varied.

The property of the dilatancy of a substance can also be used directly to increase the viscosity in situ. For this purpose, the effect of the so-called structural viscosity, opposite to dilatancy, will be explained.

Structural viscosity, also called shear thinning, is the property of a fluid to show a reducing viscosity at high shear forces. I.e., the higher the shear acting on the fluid, the less viscous, it is. Such a fluid is therefore aptly called shear thinning, which is occasionally used as a synonym for structural-viscous.

The reduction of the viscosity arises due to a structural change in the fluid which provides that the individual fluid particles (e.g. polymer chains) can slide past one another more easily.

Since the viscosity does not remain constant in a structural-viscous fluid as the shear increases, it is classified as a non-Newtonian fluid.

Other fluids from this classification have the following properties inter alia:

Dilatancy, the opposite behavior to structural viscosity;

Thixotropy, the viscosity does not immediately increase again after reduction of the shear force; Rheopexy, the opposite behavior to thixotropy.

Structural viscosity: The individual polymer chains are interlinked (=interlaced) in polymer solutions and polymer melts. As the shear force increases, these interlinks release and the viscosity drops. This effect plays a large role in the processing of thermoplastics. Lower injection pressures are therefore required in the preparation of thin-walled injection molded parts than with thick-walled ones.

Non-drip wall paint does not drip off the roller since the shear is small and the viscosity is large, whereas it is easy to apply to the wall since the thin film between the wall and the roller causes a large shear and thus the viscosity is small.

Associative materials are systems in which small molecules congregate to form supramolecular systems via physical interactions, for example hydrogen bridge bonds or ion-dipol interactions. These bonds which are weak (in comparison with covalent bonds) are broken open by shear, which lowers the viscosity. The special feature in this respect is that the bonds only completely form back after a certain material-specific time (→thixotropy). Technically important representatives are ionomers.

Dilatancy (also shear thickening) is in rheology the property of a non-Newtonian fluid to show a higher viscosity at high shear forces. A dilatants fluid is also called shear thickening or shear hardening.

The increase in the viscosity arises through a structural change in the fluid which ensures that the individual fluid particles interact more with one another (for example interlace) and so slide past one another less easily.

The viscosity of a dilatant fluid increases with the shear speed, but does not depend on the time with a constant shear speed.

If the viscosity does not immediately fall again after a reduction of the shear force, one speaks of rheopexy which is indeed time-dependent.

The US manufacturer Dow Corning produces the dilatant putty Silly Putty (also called Bouncing Putty, Thinking Putty, Smart Putty) from silicone polymer which was previously above all on the market as a children's toy. In addition to the normal kneadability, this substance behaves completely differently on a sudden mechanical strain: if a ball of the material is thrown to the ground, it bounces back up like a rubber ball; if a piece is hit very quickly with a hammer, it smashes into a number of small, sharp pieces, almost like ceramics. Sharp edges and smooth break surfaces also form on tearing apart. Technical applications were not previously known.

A material with similar properties has recently been used as an active protection system (APS), for example in motorcycle clothing: especially shaped pads which contain a dilatant compound permit the free movability of the carrier. On an abrupt blow as a consequence of a fall, however, the material "hardens" to a hard rubber-like consistency, distributes the acting forces over a larger body area and so prevents injuries.
Electrorheological Fluids (ERFs):

A distinction is made between homogeneous and heterogeneous electrorheological fluids. The homogeneous ERFs comprise e.g. aluminum salts of stearic acid. The active mechanism of the homogeneous ERFs is not known with absolute certainty. The heterogeneous ERFs comprise polarizable particles or droplets which are dispersed in an electrically non-conductive carrier fluid, e.g. silicone oil or mineral oil.

Dipoles are induced in the particles by an external electric field. The particles form chains and columns along the field lines of the electric field. This so-called Winslow chain model is the simplest structural model to explain the electrorheological effect.

Practical application and areas of use Electrorheological fluids are usually used as a central component of a mechatronic system. These systems can react to different general conditions together with a housing, a high-voltage power pack and a corresponding control or regulation.

The damping properties of hydraulic bearings can thus, for example, be controlled by the use of an electrorheological fluid in that the viscosity of the electrorheological fluid is controllable. When such a bearing is used as an engine bearing in an automobile, the damping could be matched dynamically to the speed of the engine and to the property of the ground to reduce the noise strain for the occupants. Electrorheological fluids are just as loadable as their base materials. When used as a variable brake, modern ERFs are, unlike solid brakes, not abrasive and are comparatively temperature stable. There are, however, also ERF formulations which can be used as abrasives due to their high abrasiveness.

The research and development of the past years have resulted in considerable improvements both in the rheological properties and in the electric properties of electrorheological fluids. In this respect, the development has in particular concentrated on ERFs from polymer particles. Abrasion and wear no longer play any role with these electrorheological suspensions, e.g. of polyurethane particles, dispersed in a silicone oil as a carrier. The soft and elastic particles have, on the one hand, no abrasive influence on the mechanical components of the ER systems (pumps, valves); on the other hand, they are themselves extremely resistant to mechanical wear due to their flexibility so that no degradation of the ERF itself is to be seen even under the most vigorous mechanical load.

BRIEF DESCRIPTION OF THE DRAWINGS

The invention will be shown and subsequently described in the following with reference to a plurality of embodiments in a drawing.

There are shown

FIG. 2 schematically, a blood vessel which opens into a ventricle and through which a hollow catheter having a heart pump is pushed in;

DETAILED DESCRIPTION OF THE INVENTION

Figure 1:
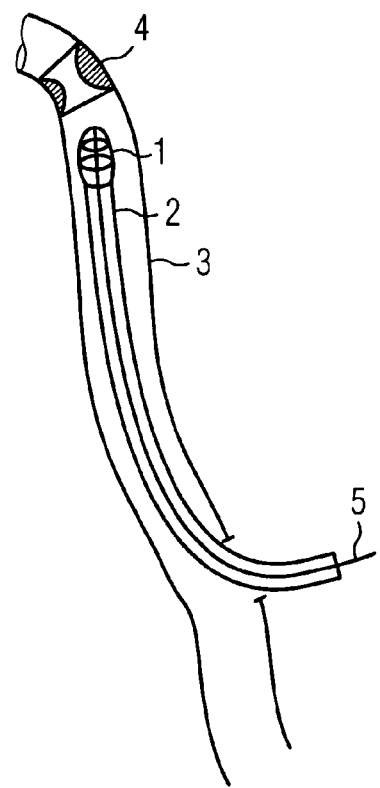
FIG. 1 schematically in a longitudinal section, a blood vessel with a hollow catheter introduced into it and a rotary cutter.

FIG. 1 shows, as an example for an apparatus in accordance with the invention, a rotary cutter 1 which is introduced at the distal end of a hollow catheter 2 into a blood vessel 3 of a human body to eliminate a constriction 4 by cutting away deposits at the wall of the blood vessel. A shaft 5 runs within the hollow catheter 2, said shaft being configured for a rotation at high speed and being able to be driven by a motor from outside the hollow catheter.

The rotary cutter 1 is advantageously first introduced into the blood vessel 3 in a transport state, for example in radially compressed form, and is then changed into an operating state on site which can, for example, differ from the transport state in that the cutter head is radially enlarged or stiffened. The invention solves the problem of effecting this change in the mechanical properties of the rotary cutter in a favorable form after passing through the transport path.

Figure 2:
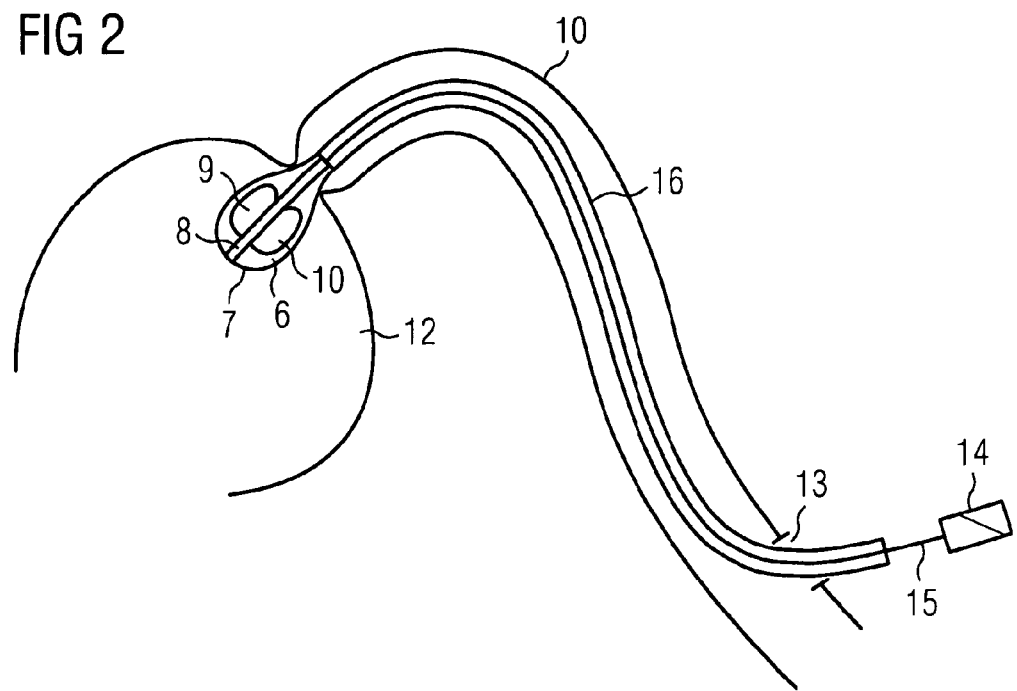

FIG. 2 shows a further example application for an apparatus in accordance with the invention which is in this case formed by a heart catheter pump 6. The latter has a housing 7 in which a rotor is accommodated which has a hub 8 and conveying elements 9, 10 in the form of conveying blades.

The pump typically has a larger diameter in operation than during the transport in order to give it the required efficiency. For this reason, the pump is radially compressed before the introduction into a blood vessel 11 through which it should be pushed into a ventricle 12. Then it is introduced through a sluice 13 into the blood vessel 10 and is pushed through up to the ventricle 12. The pump, for example the rotor and the pump housing, is then radially expanded together or each part on its own. The invention can generate the expansion movement per se or assist it. It can, however, also only become effective after the expansion movement in that, for example, the rotor or the pump housing is stiffened in the expanded position and is thus stabilized.

The pump can then be operated at high speeds and under high mechanical load in that the motor 14 drives the shaft 15 at 10,000 r.p.m., for example.

The erection of the individual elements of the pump 6 after the bringing to the deployment site in the ventricle 12 can take place, for example, in that the rotor 8, 9, 10 is set into rotation and is erected either by the acting centrifugal forces or by the counter fluid forces which are adopted on the rotation or by both together. In addition or alternatively, mechanical apparatus such as pulls or compression devices can also be provided which can be actuated along the hollow catheter 16 from outside the patient body and which act on the pump head and there cause or assist a corresponding expansion movement. Other mechanisms are also possible via which it is possible to work toward an expansion. They will be explained by way of example with reference to the other Figures.

Figure 3:
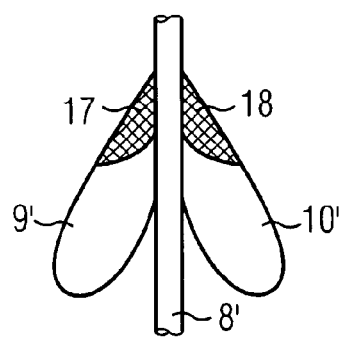
FIG. 3 a rotor or a pump in the transport state.

FIG. 3 shows a view of a rotor having conveying blades or rotor blades 9', 10' which are arranged at a hub 8' and which are still shown in the transport state in FIG. 3 in which they lie radially at the hub 8'.

A respective part region 17, 18 of each conveying element 9', 10' is designed such that it contracts through certain external influences such as radiation with UV light or particle radiation, ($\alpha$, $\beta$, $\gamma$ radiation), electric and/or magnetic fields, ultrasound or mechanical strain. Self cross-linking plastics which harden, on the one hand, and contract, on the other hand, on the cross-linking can be selected as the materials 17, 18, for example.

Figure 4:
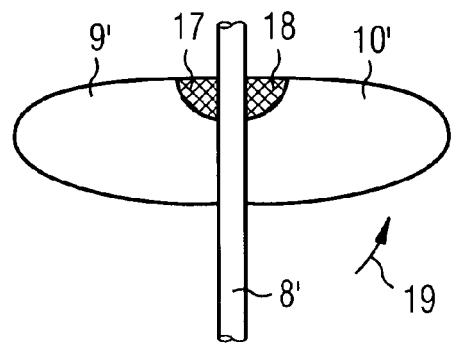
FIG. 4 the rotor of FIG. 3 in the operating state.

FIG. 4 shows that the conveying elements 9', 10' are pulled more to the hub 8' in their regions by a contraction of the regions 17, 18 and are thus radially erected, as indicated by the arrow 19. This effect is stable and permanent with a permanent cross-linking. It is, however, also conceivable to use materials which show such a contraction temporarily, for example by effects of magnetorestriction or piezoelectric effect. In the last-named case, the rotor is only radially expanded for so long as (or with an effect only in the transport state until) the corresponding fields act. Otherwise the rotor stabilizes and the external effect can be omitted without the rotor becoming unstable.

It is also conceivable to manufacture the whole region of the conveying elements in the region of the hub from a corresponding material which either contracts or stiffens, wherein the geometry has to be selected accordingly to achieve an automatic erection of the conveying elements if the erection is not achieved by another effect, for example by manipulation by means of wire pulls or similar. If the expansion is achieved by other effects, it may be sufficient to stiffen parts of the conveying elements 9', 10' or the total conveying elements in that they are manufactured from a corresponding cross-linkable material or from a material which stiffens under a corresponding effect. Elastomers already exist, for example, which react to magnetic fields by stiffening.

Figure 5:
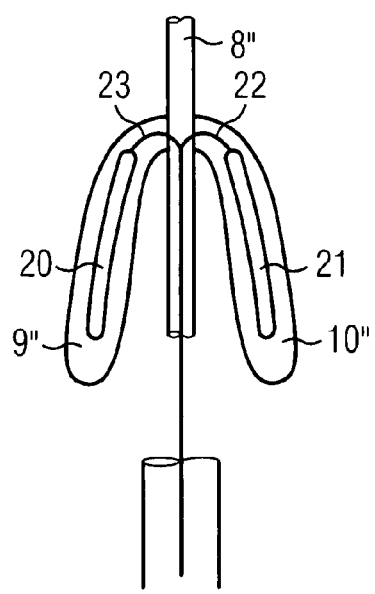
FIG. 5 a further rotor in the transport state.

A further embodiment of the invention is shown in FIG. 5 having a rotor with a hub 8" and two conveying blades 9", 10" and hollow spaces 20, 21 arranged therein.

The hollow spaces 20, 21 are connected to a pressure source via a line system having feeds 22, 23 which extend through the hub 8". Corresponding lines can be fed either through a lumen of the hollow catheter or through hoses additionally arranged inwardly or outwardly at the hollow catheter there.

Figure 6:
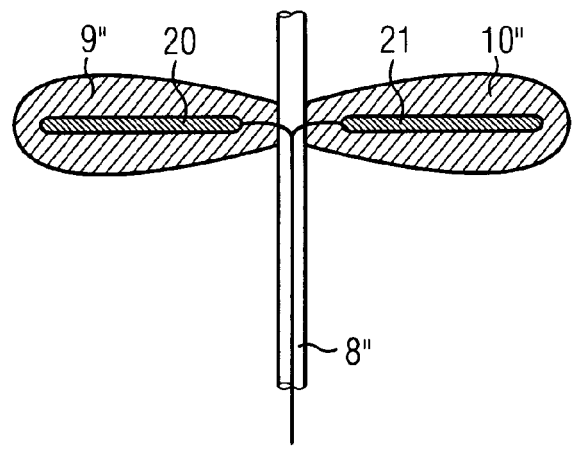
FIG. 6 the further rotor of FIG. 5 in the operating state.

A gas or a liquid can, for example, be fed into the hollow spaces 20, 21 for erecting the conveying elements 9", 10" so that the conveying elements 9", 10" are erected and tightened as shown in FIG. 6. A corresponding pressed-in liquid in the hollow spaces 20, 21 is then solidified either by cross-linking or by a chemical reaction with a further material or the properties of the liquid are changed by a field effect, which is, for example, possible with magnetorheological liquids by the effect of a magnetic field and a corresponding change in the viscosity and with electrorheological properties by electric fields. The rotor is thus stabilized and stiffened at a high viscosity of the liquid.

If a gas is first pressed in, a further substance must then be introduced to maintain the stiffening permanently. A plurality of substances can, for example, also be introduced in the form of liquids and/or gases which either react with one another after meeting in the hollow spaces 20, 21 or which are added to by a catalyst as soon as the conveying elements 9", 10" are erected to accelerate the reaction. If an irreversible reaction is triggered by the external effect, the effect can be removed after the stiffening of the rotor. On the other hand, the maintenance, for example of a field, can also be necessary to maintain the corresponding desired mechanical properties of the rotor.

The pressing of the gas into the hollow spaces can also be utilized exclusively for the erection of the conveying elements if then other elements of the rotor are stiffened for stabilizing this state.

Figure 7:
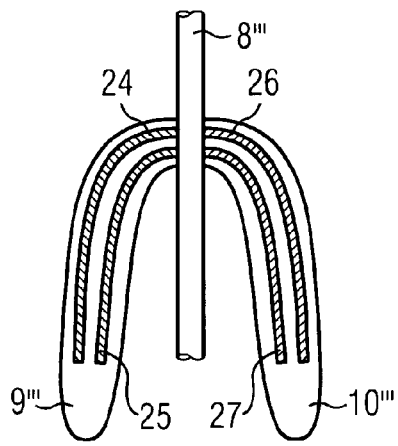
FIG. 7 a third rotor in the transport state.

FIG. 7 shows a rotor having two conveying elements in the form of impeller blades 9''', 10''', wherein each of the conveying elements has two stiffening webs 24, 25, 26, 27. They are still flaccid in the transport state of FIG. 7 so that the conveying elements 9''', 10''' can contact the hub 8'''.

Figure 8:
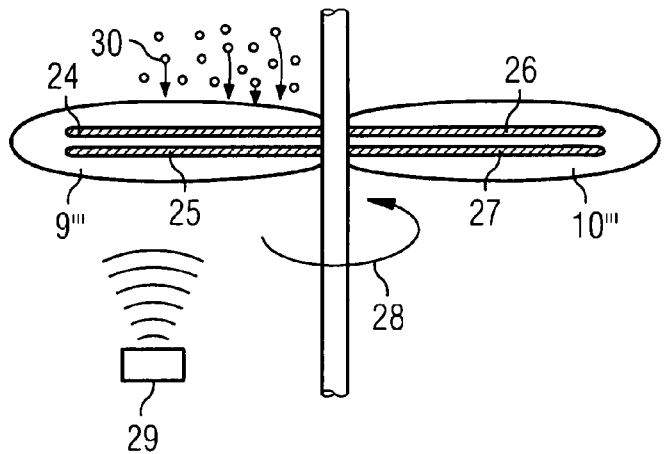
FIG. 8 the rotor of FIG. 7 in the operating state during the stiffening process.

After being brought to the deployment site, the rotor is set into rotation, as designated by the arrow 28 in FIG. 8, so that the conveying elements 9''', 10''' are erected by centrifugal force and/or fluid counter-pressure. At this time, the reaction can start for stiffening the webs 24, 25, 26, 27, either by radiation such as by means of an influencing source 29, which can, however, also be replaced by a magnetic or electric field source, or by an ultrasound source or by a chemical reaction which can be triggered or conveyed by diffusing in a substance 30 in which the conveying elements move. This substance can, for example, be present in human blood as a component of the blood in natural form before the pump is used. If this substance diffuses into the conveying elements and meets the reinforcement or stiffening webs, a hardening reaction takes place there which stiffens the conveying elements.

Figure 9:
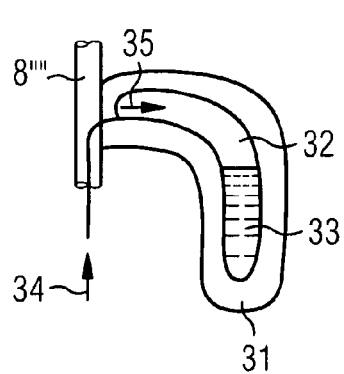
FIG. 9 a detail of a rotor with a conveying element which has a hollow space which is partially filled.

FIG. 9 schematically shows a single conveying element 31 having a hollow space 32 which is partially filled with a liquid 33.

Figure 10:
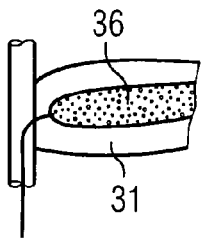
FIG. 10 the detail of FIG. 9, with the hollow space being completely filled.

Provision is made for erecting and/or stiffening the conveying element 31 that a gas flows in along the arrows 34, 34 through a lumen in the hub 8''' and the conveying element 31 into the hollow space 32 and reacts there with liquid 33 while forming a foam. An expansion by which the hollow space 32 is pressurized and inflated takes place hereby and by the corresponding reaction. At the same time, the foam 36 is stiffened, either by the reaction or by a subsequent hardening and thus stabilizes the conveying element 31, as shown in FIG. 10.

Figure 11:
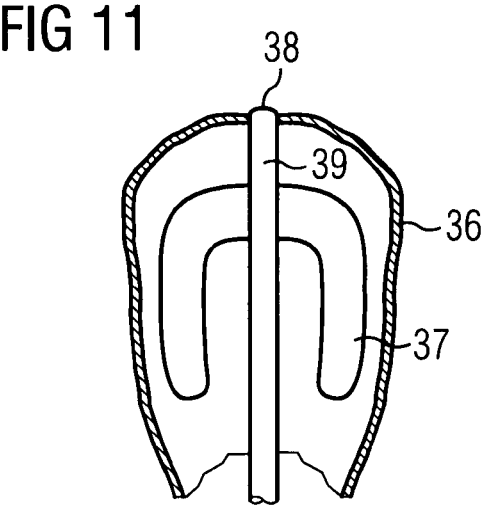
FIG. 11 schematically, a view of a rotor in the transport state with a pump housing which is collapsed.

FIG. 11 shows a pump in the transport state having a pump housing 36 in the form of a membrane which is collapsed and tightly surrounds the likewise compressed rotor having the conveying blades 37. The housing 36 is fastened to the end 38 of the hub 39 and is pushed in this state at the end of a hollow catheter through a blood vessel.

Figure 12:
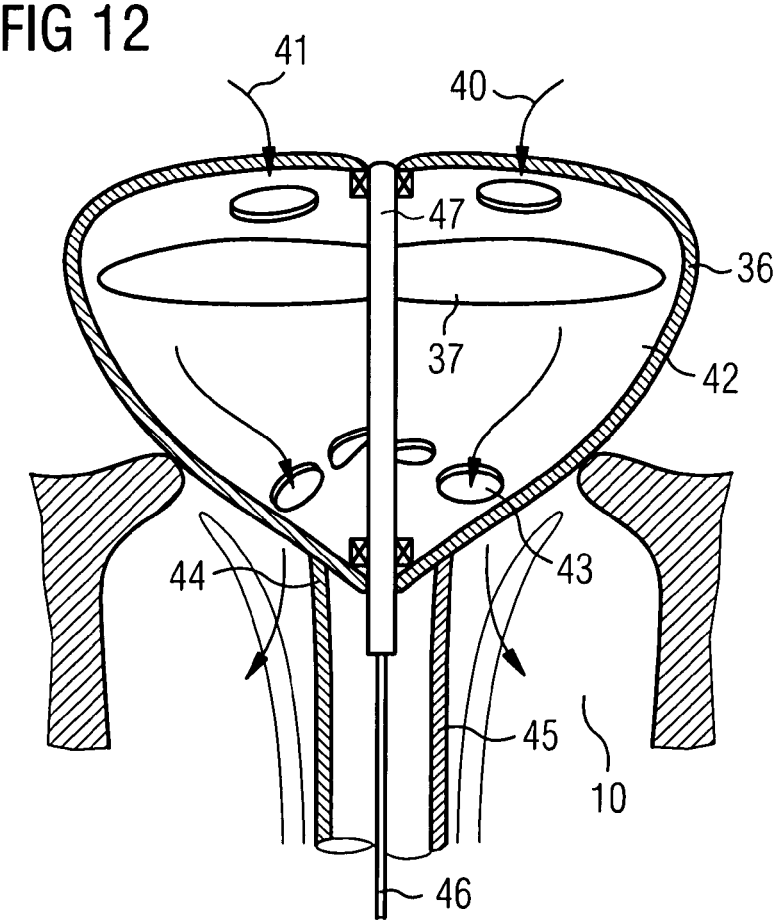
FIG. 12 the pump of FIG. 11 in the operating state.

If the pump head is pushed through the aortic arch and into a ventricle in a use as a heart pump, the rotor can slowly be set in motion, as shown in FIG. 12. The conveying blades 37 are erected by the centrifugal force and/or by fluid counter forces of the blood to be conveyed, suck blood through openings at the front side of the housing 36, indicated by the arrows 40, 41, and thus increase the pressure in the inner space of the pump housing 36. The membrane 36 is hereby widened and inflated and tautens tightly. At the same time, the space for the complete unfolding of the conveying blades 37 opens so that the rotor can take up its full rotational speed. The blood can then be pressed from the inner space 42 of the pump housing 36 through the openings 43 into the blood vessel 10.

The pump housing 36 is in this respect supported on the distal end 44 of the hollow catheter 45, with the drive shaft 46 which ends at the hub 47 also extending through the hollow catheter 45. The hub 47 is sensibly rotatably supported at both ends of the pump housing 36.

If the operating state is achieved by complete unfolding of the rotor or of the conveying blades 37 and pumping up the pump housing 36, the pump can thus be stabilized in this state by hardening both of the pump housing and of the conveying blades. This is done, for example, by radiation from outside with UV light, another radiation or ultrasound or by a chemical effect either by addition of a suitable substance starting a reaction at the conveying elements or at the pump housing or by reaction with a substance which is anyway in the blood to be conveyed and which acts as a reaction partner or as a catalyst.

Alternatively to this, a temporary stiffening or increase of the viscosity can also be provided here in the case of filling liquids by using magnetic or electric fields.

Corresponding fields can be introduced or radiated in from outside the patient's body or they can be applied by corresponding probes which are brought into the vicinity of the pump or are arranged at the end of the hollow catheter carrying the pump.

In an embodiment which can also be protected as a separate invention, a motor can be arranged at the pump head, for example with a corresponding pump, said motor generating a magnetic rotary field by means of its coil when switched on. Since said rotary field also rotates at the speed of the rotor, it represents a stationary magnetic field with respect to the impeller blades of the rotor which can therefore—in addition to the drive function—influence the magnetorheological fluid of the rotor blades in order to stabilize them. In a further embodiment, likewise protectable on its own, a coil without a drive function can also be arranged at the pump head, said coil effecting the stabilization of the corresponding rotor, wherein the rotor would be driven by a separate drive, for example by a flexible shaft.

It is also possible for all embodiments shown in this application, as well as also independently thereof, that electromagnetic radiation such as light, UV radiation, infrared radiation, short waves or X-ray radiation is, for example, conducted to the pump head to cause a hardening reaction there. This can take place, for example, via a suitable optical fiber which can be conducted, for example, through the hollow catheter.

Figure 13:
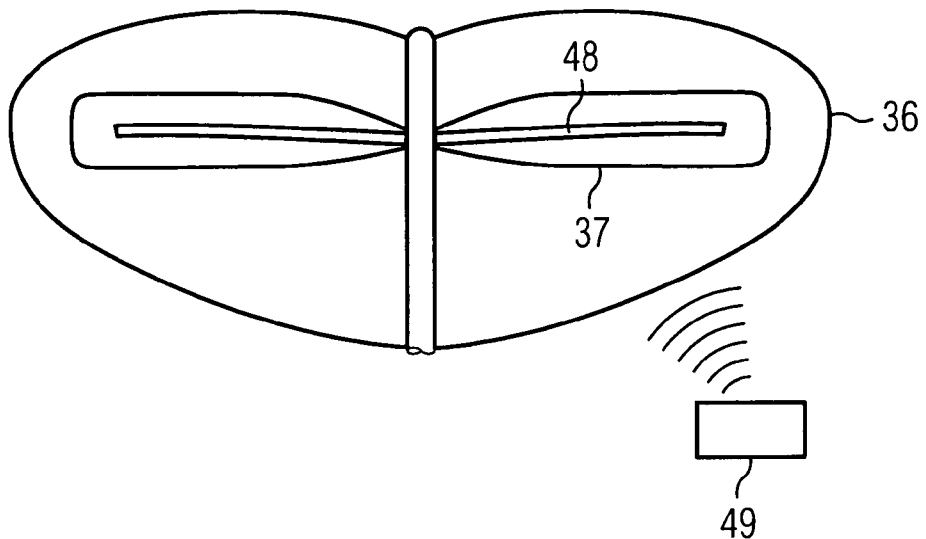
FIG. 13 a rotor in the operating state in stiffened form with a housing of a pump in the operating state.

FIG. 13 schematically shows a pump head having a housing 36 and conveying blades 37 which have reinforcing ribs 48. They are typically stiffened to stabilize the operating state, for example by cross-linking of a cross-linkable polymer.

To solve the problems which may occur in a patient on the removal of the pump head after the treatment, it is necessary to compress the conveying blades 37. This can be done, for example in that the rotor is further radiated by a radiation source 49 so that the hardening is continued by further cross-linking up the embrittlement. If the stiffening webs 48 are embrittled, they can break on their own or can be broken simply on the removal of the pump by retracting the pump head into the hollow catheter 49.

Figure 14:
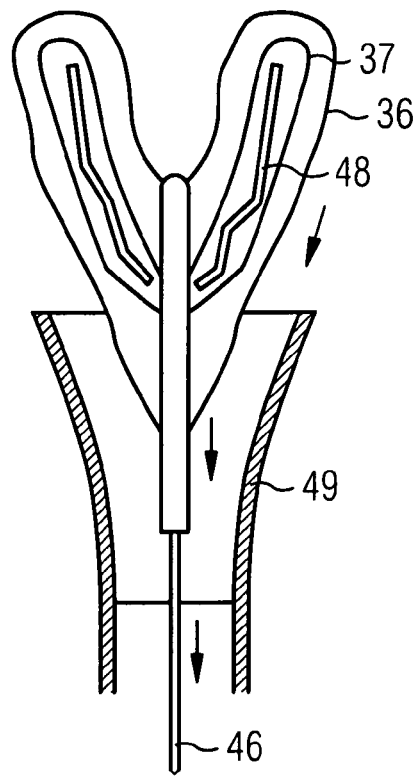
FIG. 14 the parts of the pump of FIG. 13 after a further treatment which allows the breaking of the conveying elements.

FIG. 14 shows the reinforcement webs 48 within the conveying blades 37 in the kinked or broken state, as the pump head is pulled back together with the housing 36 into the funnel-shaped distal end of the hollow catheter 49 by means of the drive shaft 46. The retraction can, however, also take place by other means such as pulls extending parallel to the drive shaft 46 in the hollow catheter 49.

In the manner described, the pump head can be pulled into the hollow catheter without any greater mechanical resistance and can be removed together with it out of the ventricle or through the blood vessel out of the patient's body.

Alternatively to the continuation of the hardening process, which was utilized after the transport to stiffen the rotor, up to the embrittlement, a treatment can also take place which is different from the initial stiffening treatment. An embrittlement or a breaking can, for example, be provided by ultrasound treatment. A temperature lowering can also be locally effected, for example, by introduction of a coolant through the hollow catheter 49 in order to embrittle the rotor and/or the pump housing and to make it susceptible to breaking. It is the most sensible in this respect accordingly only to break the rotor and to leave the pump housing intact so that any breaking splinters which may occur cannot enter into the bloodstream.

Figure 15:
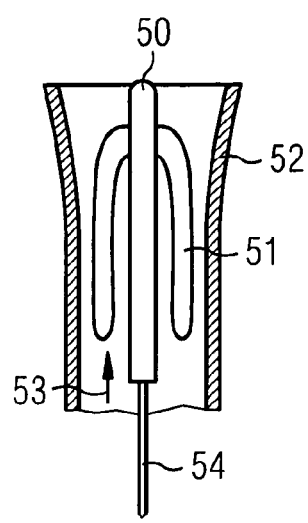
FIG. 15 a rotor with conveying elements which is pushed through a hollow catheter in the transport state.
Figure 16:
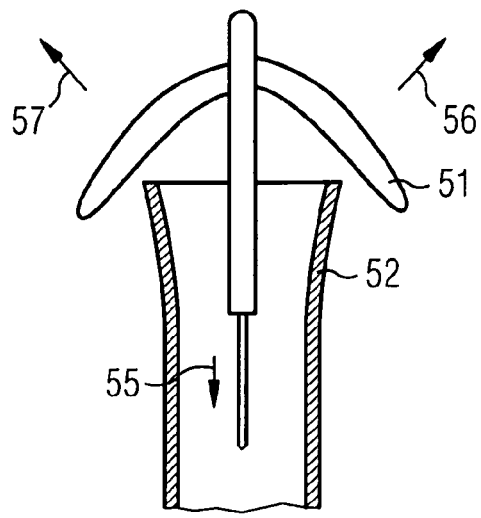
FIG. 16 the rotor of FIG. 15 which is erected by withdrawing the hub into the hollow catheter.

In FIGS. 15 and 16, a possible erection mechanism is shown for a rotor after the transport and for the transition to the operating state.

In FIG. 15, a rotor is shown having the hub 50 and the conveying blades 51 in the compressed state within the hollow catheter 52 shortly before it is pushed out of the hollow catheter within the ventricle in the direction of the arrow 53. The pushing out can take place by means of the drive shaft 54 or by means of further wires or pulls, not shown. In this state, the rotor is still unhardened and movable. Once it has been moved out of the hollow catheter, it is also alternatively or additionally possible, in addition to other possibilities of expansion, to retract the rotor subsequently a little in the direction of the arrow 55 in FIG. 16 so that the conveying blades 51 abut the edge of the distal end of the hollow catheter 52 by the abutment and are erected radially in the direction of the arrows 56, 57. A hardening of the rotor or only of the conveying blades or of parts of the conveying blades can then take place so that the rotor is stabilized in expanded form. The rotor can thereupon again be pushed out of the hollow catheter 52 in the direction of the arrow 53 and can be pushed away therefrom to reach the operating position. In the above observation, the housing of the pump has been left out of consideration; however, it will be additionally provided in the predominant number of embodiments and will surround the rotor.

Figure 17:
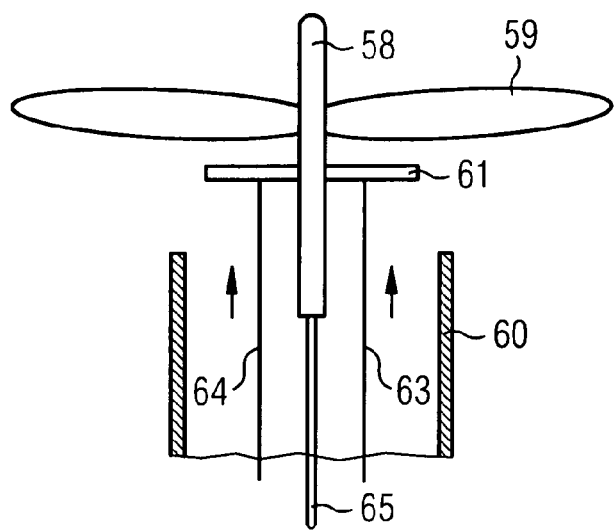
FIG. 17 a rotor which is erected by displacement of a support wheel by means of thrust elements.
Figure 18:
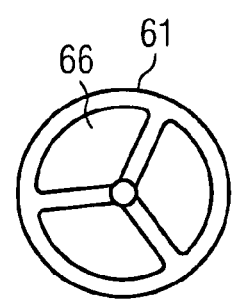
FIG. 18 a view of the thrust wheel.

FIG. 17 shows a further embodiment of a rotor having a hub 58 to which the conveying blades 59 are fastened. After the moving out of the hollow catheter 60, in a similar manner as shown in FIG. 15, the rotor or the conveying blades of the rotor can be erected by a pushing up of an erection wheel 61 which is shown more clearly in the plan view in FIG. 18. The erection wheel 61 is effected by pushing by means of a plurality of thrust elements 63, 64 or by means of a hose-like element which extends within the hollow catheter 60 and which can, for example, surround the drive shaft 65.

In the erected state of the rotor, it is then hardened and then the erection wheel 61 can be retracted into the hollow catheter 60. The erection wheel 61 is provided with large passage openings 66 in order not to impair or only minimally to impair the flow relationships of the pump.

As a supplement to all the above-named examples and also usable as an independent invention, it is moreover also possible to cause the process of the hardening and/or of the softening of the apparatus in each case by a brief effect of a pulse, of an electromagnetic field or of a similar influence so that the respective duration of influence is limited to the minimally required degree. The crystallization process of the liquid can thus, for example, be triggered by a brief mechanical pulse, similar to the procedure with so-called heat packs. The corresponding crystallized medium can then be liquefied again by a brief local heat effect. By adding to the medium metal particles, for example, which have been excited in a corresponding field, the heat effect could be locally limited so much that any damage to the surrounding tissue is reduced to a non-harmful degree or is completely avoided.

The apparatus in accordance with the invention and the methods in accordance with the invention allow the influencing of the mechanical properties of elements of an apparatus, especially a blood pump, introduced into a patient's body using a technically clear-cut effort so that said apparatus can be brought into the suitable form for operation or can be provided with the required stiffness without the corresponding mechanical properties already having to be present on the introduction into the patient's body. New design forms of corresponding apparatus/pumps thereby become possible.

The invention claimed is:

1. A pump or rotary cutter for operation in a fluid having at least one first element which can be brought from a transport state into an operating state in situ after introduction into a patient's body by changing at least one mechanical property, wherein the first element at least partly comprises a material or can be filled with a material or material mixture which passes through a material conversion by a chemical reaction, in particular cross-linking, or passes through a transition from the liquid state into a solid state for a transition into the operation state.

2. The pump or rotary cutter in accordance with claim 1, wherein the first element is a part of a rotor of a conveying element.

3. The pump or rotary cutter in accordance with claim 2, wherein the first element is a conveying blade of a pump.

4. The pump or rotary cutter in accordance with claim 1, wherein the first element is a pump housing.

5. The pump or rotary cutter in accordance with claim 1, wherein the changeable mechanical property is the stiffness and/or the geometrical form.

6. The pump or rotary cutter in accordance with claim 1, wherein the first element has a hardenable material.

7. The pump or rotary cutter in accordance with claim 6, wherein the material can be hardened by temperature effect, electric and/or magnetic fields, radiation, mechanical effect or by initializing a crystallization.

8. The pump or rotary cutter in accordance with claim 7, wherein the material can be hardened by the addition of a further material that is included in the medium on which the apparatus has an effect, or by contact with a further material.

9. The pump or rotary cutter in accordance with claim 1, wherein the first element can be changed by a continued or further reaction, reversibly or irreversibly, into a state in which the apparatus can be transported or in which it can be brought into a transport state by mechanical destruction.

10. The pump or rotary cutter in accordance with claim 1, having the at least one first element which can be brought from the transport state into the operating state by changing the at least one mechanical property, wherein the first element at least partly comprises the material or can be filled with the material or material mixture which, as long as it is exposed to a radiation, an electric field and/or a magnetic field, has mechanical properties changed with respect to the state without such effect, in particular changed stiffness/viscosity or shape.

11. A method for putting into operation an apparatus in accordance with claim 1, wherein the material/material mixture of the first element undergoes a reaction, in particular cross-linking, or a crystallization after introduction into a body of a living being before operation or directly on being switched on.

12. The method in accordance with claim 11, wherein the material is introduced into at least one hollow space of the first element before the reaction or crystallization.

13. The method in accordance with claim 12, wherein an effect is applied to the apparatus by radiation, temperature change or mechanical effect, in particular ultrasound, or by electric and/or magnetic fields to initiate, assist or carry out the reaction or crystallization.

14. The method for operating an apparatus in accordance with claim 13, wherein the apparatus is exposed to the corresponding effect after its introduction into the body of a living being and is started during said effect; or in that the apparatus is exposed to a corresponding effect during transport which is changed or ended for the transition into the operating state.

15. A pump or rotary cutter for operation in a fluid having at least one first element which can be brought from a transport state into an operating state in situ after introduction into a patient's body by changing at least one mechanical property, wherein the first element at least partly comprises a material or can be filled with a material or material mixture which passes through a material conversion by a chemical reaction, in particular cross-linking, or passes through a transition from the liquid state into a solid state for a transition into the operation state, wherein said material or material mixture is within hollow spaces within said at least one first element.

* * * * *